United States Patent [19]

Rosenstein et al.

[11] Patent Number: 4,855,240
[45] Date of Patent: Aug. 8, 1989

[54] SOLID PHASE ASSAY EMPLOYING CAPILLARY FLOW

[75] Inventors: Robert W. Rosenstein, Elliott City; Timothy G. Bloomster, Reisterstown, both of Md.

[73] Assignee: Becton Dickinson and Company, Franklin Lakes, N.J.

[21] Appl. No.: 49,328

[22] Filed: May 13, 1987

[51] Int. Cl.$^4$ ................ G01N 33/558; G01N 33/549
[52] U.S. Cl. .................................... 436/514; 422/56; 422/58; 436/518; 436/530; 436/535; 436/807
[58] Field of Search ................... 422/56, 58; 436/514, 436/518, 530, 807, 535

[56] References Cited

U.S. PATENT DOCUMENTS 4,094,647  6/1978  Deutsch et al. .
4,435,504  3/1984  Zuk et al. .
4,446,232  5/1984  Liotta .................... 436/530
4,517,288  5/1985  Giegel .................... 436/530
4,690,907  9/1987  Hibino et al. .
4,703,017  10/1987  Campbell .................... 436/518

FOREIGN PATENT DOCUMENTS

WO87/02778  5/1987  PCT Int'l Appl. ................ 436/530

Primary Examiner—Christine M. Nucker
Attorney, Agent, or Firm—Elliot M. Olstein; John G. Gilfillan, III; John N. Bain

[57] ABSTRACT

Test device and assay for determining analyte wherein tracer and sample may be simultaneously applied to different absorbent material portions both in capillary flow communication with an absorbent material portion having a binder supported thereon in a manner whereby sample contacts binder, prior to any substantial contact between sample and tracer or tracer and binder.

24 Claims, 1 Drawing Sheet

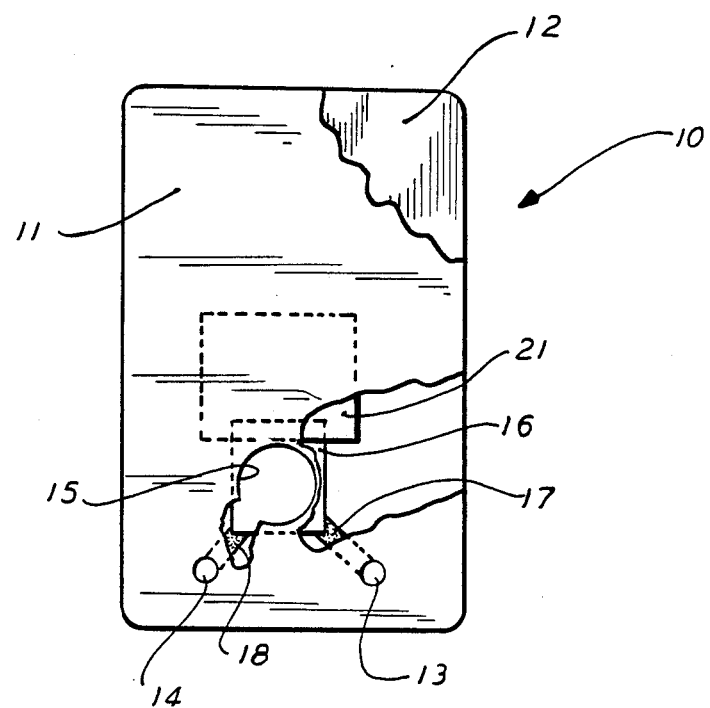

SOLID PHASE ASSAY EMPLOYING CAPILLARY FLOW

This invention relates to an assay for an analyte, and more particularly to a solid phase assay.

In a solid phase assay, a binder specific for at least the ligand to be determined (analyte) is supported on a solid support, whereby, in the assay it is not necessary to employ an additional agent for separating the bound and free phases formed in the assay.

There is known in the art assays for analytes wherein the tracer employed in the assay includes a particulate label, such as, for example, a liposome which includes a detectable marker. Thus, for example, in such an assay, a binder specific for the analyte is supported on a solid support, and the tracer is comprised of a ligand specific for the analyte, which ligand of the tracer is labeled with a particulate label, such as a liposome containing a detectable marker. In such an assay, the tracer is indirectly bound to the binder on the solid support by binding of the analyte to the binder and binding of the tracer to the analyte, whereby the presence and/or amount of analyte in a sample can be determined by detecting the presence and/or amount of tracer which is indirectly bound to the binder on the solid support.

The present invention is directed to improving assays for an analyte wherein the binder is present on a solid support, and in particular wherein the tracer employed in the assay is comprised of a ligand labeled with a particulate label.

In accordance with one aspect of the present invention, there is provided an assay for an analyte wherein there is employed in the assay a solid support having first, second and third portions, the third portion of the solid support including a binder for the analyte with the sample being applied to the first portion of the solid support and tracer to the second portion of the solid support. The first and second portions of the solid support are in capillary flow communication with the third portion of the solid support to provide for capillary flow of the sample and tracer for contact with the binder. In a preferred embodiment, the sample and tracer are caused to flow to the binder in a manner such that the sample contacts the binder, prior to substantial contact of the tracer with either of the sample or binder.

The tracer is a ligand labeled with a detectable label, preferably a particulate label, with the ligand portion of the tracer capable of being bound directly or indirectly to analyte which is bound to the supported binder.

The amount and/or presence of analyte in a sample may be determined by detecting the presence and/or amount of tracer bound to the analyte, which analyte is bound to the binder in the third portion of the solid support.

In accordance with another aspect of the present invention, there is provided a solid support having a first portion for receiving a tracer, a second portion for receiving a sample and a third portion which includes a binder for analyte in the sample wherein the first and second portions are both in capillary flow communication with the third portion to provide for flow and contact between the tracer, sample and binder. In a preferred embodiment, the capillary flow communication is such that there is contact between sample and binder prior to substantial contact of the tracer with either the sample or the binder.

In the preferred embodiment, the tracer and sample may be applied to separate portions of the solid support, without prior contact between the sample and the binder, with the sample and tracer flowing by capillary action to the third portion of the support, which contains supported binder for the analyte, in a manner such that the sample contacts the binder, prior to any substantial contact between the tracer and either of the sample or the binder, whereby a so called "sandwich assay" is accomplished, in the so called "forward" or "sequential" mode, without the necessity of separately directly applying a sample and tracer to the portion of the solid support which contains the supported binder.

The solid support includes an absorbent material capable of transporting a liquid by capillary flow. In this manner, the tracer and sample which are applied to separate portions of the support are transported by capillarity to the portion of the support which includes immobilized binder. As hereinabove indicated, the portion of the support to which the sample is applied, and the portion to which the tracer is applied are both in capillary flow communication with the portion of the support containing the immobilized binder in a manner such that the sample contacts the binder prior to substantial contact of the tracer with either the sample or the supported binder. Such a result may be achieved by appropriately arranging the respective portions of the support to which the sample and tracer are applied, with respect to the portion of the support to which the binder is applied, in manner such that the path of travel of the sample to the binder is shorter than the path of travel of the tracer to the binder. In a preferred embodiment, the tracer has a detectable particulate label whereby the tracer, having a particulate label, moves at a slower rate than the sample, and such difference in flow rate, as well as any difference in flow path, aids in providing for contact of the sample with the binder, prior to contact of the tracer with either the sample or the binder. It is to be understood, however, that the length of the flow path of the tracer may be the same as or less than the length of the flow path of the sample to the binder in that it is possible to provide for prior contact of the sample with the binder by means other than the length of the respective flow paths.

Thus, for example, a blocking agent may be added to the portion of the solid support which provides a capillary flow path between the portion of the support to which the tracer is applied, and the portion of the support which includes the binder to thereby impede the flow of the tracer to the binder. Such a blocking agent is a material which inhibits wetting of the support, with such inhibition of wetting reducing the rate at which the liquid containing the tracer flows by capillarity to the portion of the support including the supported binder. As representative examples of such blocking agents, there may be mentioned: bovine serum albumin, alone, or in combination with glucose; other proteinacious matter alone, or in combination with a sugar, such as for example, a fish gelatin obtained from a fresh water fish in combination with sucrose; and the like. The selection of a suitable blocking agent which inhibits wetting of the absorbent material to reduce the rate of flow should be apparent to those skilled in the art from the teachings herein.

As further alternatives, the respective rates of flow may be controlled by the width of the respective flow paths or the area to which tracer and sample are applied.

It is also to be understood that a combination of various means may be employed to insure that the sample applied to the solid support reaches the binder, prior to contact between the tracer and the binder, such as, for exmaple, a combination of respective lengths of flow path and the use of a blocking agent to inhibit the flow of the tracer.

Applicant has also found that substantial contact between the tracer and the sample, prior to contacting of the binder with the sample, should also be prevented. Applicant has found that prior contact between the sample and the tracer, on the solid support, may reduce sensitivity and/or may cause agglutination of the tracer in the preferred embodiment where the label of the tracer is a particulate label, whereby the sample and the tracer are applied to the separate portions of the solid support, which are in capillary flow communication with the portion of the support containing the binder, in a manner such that substantial contact between the tracer and the sample is avoided, prior to contacting of the sample with the binder. Such a result may be achieved by causing the sample to flow to the binder, ahead of the tracer, as hereinabove indicated. In addition, prevention of contact between sample and tracer prior to contact with the binder may be further assured by providing separate paths of flow for each of the sample and tracer.

Thus, the solid support is constructed and/or the portions to which the tracer and sample are applied are arranged in a manner such that both the tracer and the sample flow by capillary action to the portion of the support which includes the binder and in a manner such that the sample contacts the binder prior to any substantial contact of the tracer with either the binder or the sample. Such a result may be achieved by arranging the respective flow paths and/or flow rates of the sample and tracer on the support to achieve such a result, whereby both the sample and tracer may be applied to the support without the necessity of separately directly adding both sample and tracer to the portion of the support containing the immobilized binder.

At least the portion of the support which provides the capillary flow paths for the tracer and sample is formed from a suitable absorbent material which is capable of transporting a liquid by capillarity. As representative examples of such materials, there may be mentioned: glass fiber, cellulose, nylon, crosslinked dextran, various chromatographic papers, nitrocellulose, etc. The selection of a suitable material is deemed to be within the scope of those skilled in the art from the teachings herein.

In accordance with a particularly preferred embodiment, the portion of the support which includes the binder (third portion) is employed as the test area for determining bound tracer. In accordance with the particularly preferred embodiment, at least the third portion of the support is formed from a material which is capable of transporting material by capillary flow through such third portion and which has a surface area capable of supporting the binder in a concentration of at least 1 ug/cm$^2$ (most generally in a concentration of at least 10 ug/cm$^2$).

Although nitrocellulose is a preferred material, it is to be understood that other materials having a surface area sufficient for supporting the binder in a concentration as hereinabove described may also be employed for producing such solid supports.

In accordance with a particularly preferred embodiment, the pore size of the solid support is such that the preferred tracer (ligand labeled with a particulate label), when bound directly or indirectly to the analyte bound to the binder, remains on the surface of the support.

As should be apparent, portions of the support (or all of the support) in addition to the portion of the support employed for supporting the binder may be formed from a material having a surface area capable of supporting the binder in the hereinabove described concentrations.

The type of binder which is used in the assay is dependent upon the analyte to be assayed. As known in the art, the binder which is supported may be an antibody including monoclonal antibodies, an antigen, a protein specific for the material to be bound or a naturally occurring binder. If the assay is for an antibody, then the binder may be, for example, an antigen or an antibody which is specific for the antibody to be assayed. If the analyte is an antigen (an antigen having more than one determinant site), then the binder may be an antibody or naturally occurring binder which is specific for the antigen to be assayed.

The selection of a suitable binder for support on the solid substrate is deemed to be within the scope of those skilled in the art from the teachings herein.

The ligand which is labeled for use as a tracer in the assay of the present invention is dependent upon the analyte to be assayed, as well as the assay procedure.

Thus, for example, the ligand may be specific for the analyte, whereby the tracer would be bound directly to the analyte which is bound to the supported binder. Alternatively, the ligand employed in forming the tracer may be one which is capable of being bound to an analyte specific for the analyte; e.g., the ligand tracer may be IgG labeled with a particulate label, whereby the tracer is indirectly bound to the analyte through an antibody bound to the analyte. As should be apparent, the ligand used in producing the tracer may be an antigen or an antibody or a naturally occurring substance which is specifically bound by the analyte. The selection of a suitable ligand is within the scope of those skilled in the art.

As hereinabove indicated, in producing the tracer, the ligand is preferably labeled with a particulate label, which includes a detectable marker. In accordance with a preferred embodiment, the particulate label is visible. A preferred particulate label is a sac, which includes a dye or other colored substance as a marker, whereby the tracer, when used in the assay, is visible without destruction of the sac to release the colored substance.

The sac which is used to label the ligand for producing a tracer may be any one of a wide variety of sacs, including but not limited to intact erythrocytes, erythrocyte ghosts, liposomes (single walled [sometimes called vesicles] or multilamellar), polymer microcapsules (for example, those made by coaservation, or interfacial polymerization), etc.

Erythrocyte ghosts are known in the art and are prepared by suspending erythrocyte cells in a solution of substantially lower osmolarity. The ghosts are "resealed" in an aqueous solution including the marker whereby the ghosts include the marker in the interior thereof. Such procedures are known in the art and the resealing solution of appropriate osmolarity generally includes, in addition to the marker, alkali and alkaline earth metal halides and coenzyme; e.g., adenosine triphosphate. The preparation of ghosts, as sacs, is disclosed, for example, by D'Orazio et al, *Analytical Chemistry*, Vol. 49, No. 13, pages 2083-2086 (Nov. 1977).

Polymer microcapsules are also produced by procedures known in the art except that the solution in which the microcapsules are formed also includes the marker whereby the interior of the polymer microcapsule includes the marker. The preparation of such microcapsules is disclosed for example in *Microcencapsulation Process and Applications*, edited by Jan E. Vandegger (Plenum Press 1974).

As known in the art, liposomes can be prepared from a wide variety of lipids, including phospholipids, glycolipids, steroids, relatively long chain alkyl esters; e.g., alkyl phosphates, fatty acid esters; e.g., lecithin, fatty amines and the like. A mixture of fatty materials may be employed, such as a combination of neutral steroid, a charged amphiphile and a phospholipid. As illustrative examples of phospholipids, there may be mentioned: lecithin, sphingomyelin, dipalmitoyl, lecithin, and the like. As representative examples of charged amphiphilic compounds, cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g., dicetyl phosphate, stearyl amine, hexadecyl amine, dilauryl phosphate, and the like.

The liposome sacs are prepared in an aqueous solution including the marker whereby the sacs will include the marker in the interior thereof. The liposome sacs are easily prepared by vigorous agitation in the solution, followed by removal of marker from the exterior of the sac.

Further details with respect to the preparation of liposomes are set forth in U.S. Pat. No. 4,342,826 and PCT International Publication No. WO80/01515, both of which are hereby incorporated by reference.

As hereinabove indicated, the marker preferably included in the sac is a dye or some other material which is visible, without lysing of the sacs.

The tracer comprised of ligand and particulate label may also be produced by labeling the ligand with an aqueous dispersion of a hydrophobic dye or pigment, or of polymer nuclei coated with such a dye or pigment. Such labels are described in more detail in U.S. Pat. No. 4,373,932, which issued on Feb. 15, 1983. The tracers produced in accordance with such patent may also be employed as tracers in the present invention.

As indicated in the aforesaid patent, the colored organic compounds which are used as labels are in the form of a hydrophobic sol, which hydrophobic organic dyes or pigments are insoluble in water or soluble only to a very limited extent. As indicated in the patent, particles of the aqueous dispersion of a hydrophobic dye or pigment, or of polymeric nuclei coated with such a dye or pigment have a particle size of at least 5 nm, and preferably at least 10 nm.

Such tracers which are labeled with the hyrophobic dye or pigment or with a polymer nuclei coated with such dye or pigment, are visible tracers when used in the assay in accordance with the present invention.

The visible particulate label may be visible polymer particles, such as colored polystyrene particles, preferably of spherical shape.

As representative examples of other particulate labels which may be employed in producing a tracer for use in the assay of the present invention, in which the tracer would be visible, there may be mentioned; ferritin, phycoerythrins or other phycobili-proteins; precipitated or insoluble metals or alloys; fungal, algal, or bacterial pigments or derivatives such as bacterial chlorophylls; plant materials or derivatives and the like.

The ligand may be labeled with the particulate label so as to produce a tracer for use in the invention by procedures generally known in the art, with the procedure which is used being dependent upon the ligand and the particulate label which is employed. Such techniques include absorption, covalent coupling, derivatization or activation, and the like. In producing a tracer wherein the ligand is labeled with a sac, the sac may be produced from a component which has been derivatized with a ligand, whereby the sac, when produced, is sensitized with the ligand. In another procedure, the sac including the marker may be initially formed, followed by sensitizing the sac with ligand by procedures known in the art.

Thus, the preferred tracer is comprised of a ligand and a particulate label (solid or solid-like, as opposed to non-solid labels, such as radiostopes, enzymes and various fluorescent materials), and the particulate label preferably provides a tracer which is visible under the assay conditions so that the presence and/or amount of analyte may be determined without further treatment and without the use of instrumentation; e.g., by use of a liposome containing a dye as the particulate label.

The solid substance employed in the assay is preferably in sheet form, with the substrate, in sheet form, generally being in the form of a card, a test strip or dipstick, etc. It is to be understood, however, that other forms are also within the spirit and scope of the invention.

The binder is supported on the test area of the solid substrate by applying a solution of the binder to a defined area of the test substrate; such as, for example, in the form of a spot, which can be located in a marked area, e.g., square or circle, on the substrate. Particularly good results have been obtained when the binder is applied to the test area as a spot having a diameter of from 3 to 5 mm. The concentration of the binder placed in the defined test area will vary depending upon the assay to be performed; however, the binder is generally present in a concentration of at least 1 ug/cm$^2$ (most generally at least 10 ug/cm$^2$.)

After application of the binder to one or more test areas on the substrate, the residual binding capacity of the test substance is saturated or blocked by treatment of the test substrate with one or more types of proteins which do not specifically bind the materials to be employed in the assay. Thus, for example, the residual binding capacity of the substrate may be blocked so as to prevent non-specific binding by the use of bovine serum albumin. The techniques for preventing non-specific binding are generally known in the art, and such techniques are also generally applicable to preventing non-specific binding in the assay of the present invention.

In accordance with the present invention, the first portion of the solid support may be provided with the tracer, during the assay procedure, or the solid support may be produced with the tracer on the first portion thereof. In the latter case, the tracer is supported on the support in a manner such that upon wetting of the first portion, the tracer flows by capillarity to the third portion of the solid suport. Thus, for example, the tracer may be absorbed on the solid support, in the first portion thereof, whereby upon wetting of the first portion during the assay, th tracer flows by capillarity to the third portion of the solid support which includes the binder, as hereinabove described.

The invention will be further described with respect to embodiments thereof illustrated in the accompanying drawings wherein:

Referring to FIG. 1, there is shown a test card 10, which is generally comprised of an upper card member 11 and a lower card member 12. The upper card member 11 is provided with a tracer loading port 13, sample loading port 14 and a test view window or port 15. A test sheet 16, preferably nitrocellulose, is placed between the upper and lower card members 11 and 12, respectively, with a portion of the nitrocellulose being visible through test portion 15. At least a portion of the sheet 16 which is viewable through window 15 includes a binder specific for the analyte to be assayed and defines a test area. A first strip of absorbent material 17 is placed between the upper and lower card members 11 and 12 extends between tracer loading port 13 and view window 15 with the absorbent material 17 being in contact with test sheet 16. A second strip of absorbent material 18 is placed between the upper and lower card members 11 and 12 and extends between sample loading port 14 and view window 15, with the absorbent material 18 being in contact with the test sheet 16. As shown, the strips 17 and 18 are separate and distinct from each other and provide separate capillary flow paths from each of ports 13 and 14 to view window 15. Strips 17 and 18 may be formed, for example, from glass fiber.

As particularly shown, the sample loading port 14 is closer to the viewing window 15 than the tracer loading port 13, whereby the capillary flow path between ports 14 and 15 is shorter than the capillary flow path between ports 13 and 15. In addition, the strip 17 may be treated with a material to reduce the capillary rate of flow.

A piece of material 21 having a high liquid absorption capacity, such as blotting paper, is positioned between upper and lower card member 11 and 12 in contact with test sheet 16 to receive and store test material.

In an assay, a sample to be assayed is applied through test port 14 and tracer is applied through test port 13. The sample flows to the test sheet 16 through strip 18 and the tracer flows to test sheet 16 through strip 17. As hereinabove indicated, the flow paths and/or strips are constructed in a manner such that the sample contacts the binder on the test sheet 16, prior to contact of the tracer with either the binder or sample. The tracer may then be determined through test window 15. The presence and/or amount of analyte present in the sample may be determined by the presence and/or amount of tracer, as determined through window 15 of the card 10.

In accordance with a preferred embodiment, as hereinabove described, by using an appropriate material as sheet 16 (for example, nitrocellulose) and a visible particulate label (such as a liposome including a suitable dye), it is possible to determine tracer through window 15 without destruction of the liposome.

Although the embodiment has been described with respect to the use of a tracer which includes a visible particulate label, it is to be understood that other detectable labels may be employed within the spirit and scope of the invention; e.g., an enzyme label; a chromogen label (fluorescent and/or absorbing dye), etc. In such cases, it may be necessary to add an additional substance in order to detect the label in view window 15; e.g., in the case of an enzyme label, a substrate to produce detectable color in the view window.

It is also possible to provide a view window over the material 21 in place of or in conjunction with the view window 15. In this manner, tracer which has not been bound in test sheet portion 16 may be determined. The presence and/or amount of tracer in portion 21 may be employed to determine analyte alone and/or in conjunction with the presence and/or amount or analyte in portion 16.

The invention will be further described with respect to the following example; however, the scope of the invention is not to be limited thereby:

EXAMPLE

A reaction card 10 was constructed using two plastic cards 11 and 12. The cards were made of polypropylene with a thickness of approximately 0.03 inches. The top card has three holes which include a view window 15, liposome tracer loading port 13, and a sample loading port 14. The view window has a diameter of approximately 12.0 mm while the loading ports are smaller (4.0 mm).

The first step in construction was to place double stick adhesive (3M Type 960) over the entire card. Nitrocellulose (5.0 $\mu$S&S) with the capture antibody was attached to the card as test sheet 16. Sheet 16 was spotted with 3 ul of affinity purified rabbit anti-Group A Streptococcus antigen and then blocked with 3% bovine serum albumin. The antibody portion is below window 15. Blotting paper 21 (Gelman 51334) was placed on the card such that the paper was in contact with the nitrocellulose. The window and loading ports were punched out of a second card. Adhesive was placed over the holes and excess adhesive was removed from the holes. This process led to a card that had adhesive completely surrounding the ports. Next, strips of glass fiber (Whatman GF/A) 17 and 18 were placed on the card such that they made a connection from the loading ports to the view window. Strip 18 is treated with a 3% BSA solution.

Detector liposomes packed with sulfo-rhodamine dye were prepared by the method outlined in O'Connell et al. (Clin. Chem. 31:1424 [1985]). They were covalently coupled to affinity purified rabbit anti-Group A Streptoccus antigen.

Group A Streptococcus organisms were harvested from culture plates, washed with saline (0.9% NaCl), and adjusted to $1 \times 10^9$ organisms/ml. An aliquot (0.1 ml) containing $1 \times 10^8$ organisms were subjected to the micro nitrous acid extraction method for exposing the Group A carbohydrate antigen. This method consists of mixing 0.3 ml of 0.1M HCl with 40 ul of 4M $NaNO_2$, adding this to the Streptococcus organisms and, after 3 minutes, neutralizing with 40 ul of 1M Tris base. To facilitate the extraction, the HCl and the subsequent diluting fluid contain 0.1% Tween-20 non-ionic detergent.

A reservoir was attached to the device to assure that all the sample (0.3 ml) could be added at one time. Immediately after addition of the sample through port 14 the liposome tracer was added to the tracer port 13. No other manipulations were required. Within five minutes a specific signal at the capture antibody spot (Window 15) could be seen at a sensitivity level equivalent to $1 \times 10^6$ CFU/ml.

The present invention is advantageous in that it is possible to provide a sandwich assay without separate incubation and wash steps, and which has the requisite sensitivity.

These and other advantages should be apparent to those skilled in the art.

Numerous modifications and variations of the present invention are possible in light of the above teachings and, therefore, within the scope of the appended claims, the invention may be practised otherwise than as particularly described.

What is claimed is:

1. An assay for determining analyte in a sample, comprising:

employing a absorbent solid support having first, second and third portions, said first portion receiving a sample to be assayed, said second portion receiving a tracer, said third portion including a binder for the analyte, said third portion being in capillary flow communication with both the first and second portions; moving tracer and sample by capillary flow across the binder in the third portion to provide contact between sample and binder prior to substantial contact of the tracer with either the binder or sample; and determining at least one of tracer bound in said third portion or tracer which passes across said third portion to thereby determine analyte.

2. The assay of claim 1 wherein tracer is added to the second portion of the support during the assay.

3. The assay of claim 1 wherein tracer is present on the second portion of the support prior to the assay.

4. The assay of claim 1 wherein the tracer is comprised of a ligand and a particulate label.

5. The assay of claim 4 wherein the particulate label is a liposome including a colored substance.

6. The assay of claim 5 wherein the tracer and sample move by capillary flow to the third portion through separate and distinct flow paths.

7. The assay of claim 6 wherein the binder is supported on nitrocellulose.

8. The assay of claim 6 wherein the binder is supported on a porous material in the third portion of said support, said porous material supporting the binder in a concentration of at least 1 ug/cm$^2$.

9. The assay of claim 8 wherein the ligand portion of the tracer is bound by analyte.

10. The assay of claim 8 wherein the first, second and third portions are substantially in the same plane.

11. The assay of claim 1 wherein said solid support is a strip.

12. The assay of claim 11 wherein said strip is formed from separate pieces of absorbent material.

13. The assay of claim 1 wherein said solid support includes a blocking agent to retard the flow of tracer from the second portion to the third portion.

14. The assay of claim 1 wherein in the direction of flow said first portion is closer to the third portion than said second portion.

15. The assay of claim 1 wherein said first, second and third portions are in substantially the same plane.

16. An article of manufacture for determining analyte, comprising:

a solid support having first, second and third portions, said first portion for receiving a sample to be assayed, said second portion for receiving a tracer, said third portion including a binder for the analyte, said third portion being in capillary flow communication with both the first and second portions whereby sample and tracer flow across the binder in the third portion to provide contact between sample and binder prior to substantial contact of the tracer with either the binder or sample, said solid support being an absorbent material which provides for capillary flow.

17. The article of claim 16 wherein the first absorbent material portion defines a first flow path for capillary flow between the sample receiving portion and the third portion including the binder, and the second absorbent material portion defines a second flow path for capillary flow between the tracer receiving portion and the third portion including the binder.

18. The article of claim 17 wherein the flow path between the sample receiving portion and the third portion is shorter than the flow path between the tracer receiving portion and the third portion.

19. The article of claim 17 wherein the second absorbent material portion is treated with an agent to inhibit wetting thereof to reduce the rate of flow between the tracer receiving portion and third portion.

20. The article of claim 17 wherein the support includes an absorbent material in contact with the third portion to receive and store any sample and tracer which flows through the third portion.

21. The article of claim 17 wherein the support is a test card having a top portion and a bottom portion, the first, second and third absorbent material portions being between the top and bottom portions of the test card, said top portion including a first port over the sample receiving portion of the first absorbent material portion for application of sample thereto, a second port over the tracer receiving portion of the second absorbent material portion for application of tracer thereto, and a viewing port over the binder portion of the third absorbent material portiton to view tracer during an assay.

22. The article of claim 21 wherein the first, second and third absorbent material portions are in substantially the same plane.

23. The article of claim 17 wherein binder is supported in the third portion in a concentration of at least 1ug/cm$^2$.

24. The article of claim 16 wherein the first, second and third portions are in substantially the same plane.

* * * * *